United States Patent
Pschichholz

(10) Patent No.: US 9,008,985 B2
(45) Date of Patent: Apr. 14, 2015

(54) AUTOMATIC TEST METHOD FOR AN INSPECTION DEVICE

(75) Inventor: Manfred Pschichholz, Kamen (DE)

(73) Assignee: KHS GmbH, Dortmund (DE)

( * ) Notice: Subject to any disclaimer, the term of this patent is extended or adjusted under 35 U.S.C. 154(b) by 725 days.

(21) Appl. No.: 13/320,294

(22) PCT Filed: Jun. 2, 2010

(86) PCT No.: PCT/EP2010/003364
§ 371 (c)(1),
(2), (4) Date: Nov. 14, 2011

(87) PCT Pub. No.: WO2011/020520
PCT Pub. Date: Feb. 24, 2011

(65) Prior Publication Data
US 2012/0059615 A1    Mar. 8, 2012

(30) Foreign Application Priority Data
Aug. 18, 2009  (DE) .......................... 10 2009 037 779

(51) Int. Cl.
| | | |
|---|---|---|
| G01M 9/00 | (2006.01) | |
| G05B 9/00 | (2006.01) | |
| G06F 17/40 | (2006.01) | |
| G06F 19/00 | (2011.01) | |
| B65C 9/40 | (2006.01) | |
| B67B 3/26 | (2006.01) | |
| B67D 3/00 | (2006.01) | |
| G01M 99/00 | (2011.01) | |
| G01N 21/90 | (2006.01) | |
| G01N 21/93 | (2006.01) | |

(52) U.S. Cl.
CPC ... B65C 9/40 (2013.01); G05B 9/00 (2013.01); G06F 19/00 (2013.01); G01M 99/00 (2013.01); *B67D 3/007* (2013.01); *B67B 3/26* (2013.01); *G06F 17/40* (2013.01); *B65C 2009/402* (2013.01); *G01N 21/90* (2013.01); *G01N 21/93* (2013.01)

(58) Field of Classification Search
CPC ........ B65C 9/00; B65C 9/40; B65C 2009/00; B65C 2009/40; B65C 2009/402; B65C 2009/407; B67B 3/00; B67B 3/26; B67C 3/00; B67C 3/007; G01D 7/00; G01D 9/00; G01D 18/00; G01D 21/00; G01M 99/00; G01N 21/00; G01N 21/84; G01N 21/88; G01N 21/90; G01N 21/93; G01N 2021/00; G01N 2021/01; G01N 2021/90; G05B 9/00; G05B 9/02; G05B 15/00; G05B 15/02; G05B 23/00; G05B 23/02; G06F 11/00; G06F 11/30; G06F 11/32; G06F 11/34; G06F 15/00; G06F 15/16; G06F 17/00; G06F 17/10; G06F 17/40; G06F 19/00
USPC ............ 73/432.1, 865.8, 865.9, 866.3; 209/3, 209/3.1, 3.2, 506, 522, 523, 524, 526, 528, 209/529, 552, 576, 577, 597; 250/200, 250/559.01, 559.4, 559.44, 559.45; 356/72, 356/73, 237.1, 237.2, 237.5, 240.1, 402, 356/426; 382/100, 112, 141, 142, 143, 152; 700/1, 90, 95, 108, 109, 110; 702/1, 702/81, 82, 83, 84, 127, 182, 183, 187, 702/189; 708/100, 105, 200
See application file for complete search history.

(56) References Cited

U.S. PATENT DOCUMENTS

| | | | | |
|---|---|---|---|---|
| 2,602,586 | A * | 7/1952 | Davidson | 702/81 |
| 2,721,701 | A * | 10/1955 | Hardesty et al. | 377/16 |
| 2,767,914 | A * | 10/1956 | Merrill et al. | 702/82 |
| 3,082,871 | A * | 3/1963 | Duncan | 209/548 |
| 4,593,369 | A * | 6/1986 | Thompson | 702/82 |
| 4,619,133 | A | 10/1986 | Kautz et al. | |
| 5,753,508 | A | 5/1998 | Robertson et al. | |
| 6,523,328 | B1 * | 2/2003 | De Cardenas et al. | 53/53 |
| 6,910,313 | B2 * | 6/2005 | De Cardenas et al. | 53/53 |
| 7,340,086 | B2 | 3/2008 | Werzinger | |
| 7,509,786 | B2 | 3/2009 | Thatenhorst | |
| 2004/0020163 | A1* | 2/2004 | De Cardenas et al. | 53/53 |
| 2004/0237472 | A1* | 12/2004 | De Cardenas et al. | 53/399 |

| | | | |
|---|---|---|---|
| 2005/0263443 | A1 | 12/2005 | Martin |
| 2009/0316145 | A1 | 12/2009 | Widera |
| 2011/0164257 | A1 | 7/2011 | Motter et al. |

FOREIGN PATENT DOCUMENTS

| | | |
|---|---|---|
| DE | 3324449 | 1/1985 |
| DE | 3330817 | 3/1985 |
| DE | 4302656 | 5/1994 |
| DE | 4441245 | 5/1996 |
| DE | 19602655 | 7/1997 |
| DE | 10065321 | 7/2002 |
| DE | 102004005994 | 9/2005 |
| DE | 102006022492 | 11/2007 |
| DE | 102008050249 | 4/2010 |
| EP | 0722789 | 7/1996 |
| EP | 1281446 | 2/2003 |
| EP | 2186736 | 5/2010 |
| WO | 93/13879 | 7/1993 |

* cited by examiner

*Primary Examiner* — Edward Cosimano

(74) *Attorney, Agent, or Firm* — Occhiuti & Rohlicek LLP

(57) ABSTRACT

The invention relates to a test method for examining an inspection device, which is associated with a functional unit of a master unit, comprising at least the following steps: producing a specified number of faulty and/or correct containers or test containers by means of the functional unit itself in that a control signal for producing a distinctive element is fed to the functional unit; leading the faulty containers or test containers past the inspection device, which detects the faulty containers or test containers and produces a signal to discharge the faulty containers or test containers, or indicates a value regarding the expected and the measured faulty and/or correct containers. The test method is automatically started or performed and is suitable, for example, for examining a label position checking device, the filling amount checking unit, and the closure seating checking unit in order to be able to determine the fault-free functioning thereof or optionally the faulty functioning thereof. The test method is characterized in that operation is not required. The test method is characterized in that the test method allows clear and documented rules for the procedure and the test results, which ensure quality control in terms of product liability.

15 Claims, 2 Drawing Sheets

PRIOR ART

AUTOMATIC TEST METHOD FOR AN INSPECTION DEVICE

CROSS REFERENCE TO RELATED APPLICATIONS

This application is the national stage application of international application no. PCT/EP2010/003364, filed Jun. 2, 2010, which claims the benefit of the priority date of German application no. 10 2009 037 779.4, filed Aug. 18, 2009. The contents of both applications are incorporated herein by reference.

FIELD OF INVENTION

The invention relates to a test method for examining an inspection device that is associated with a functional unit of a master unit.

BACKGROUND

DE 10 2004 005 994 A1 discloses a labeling machine having an apparatus for feeding of labels, and a labeling unit. The labeling unit has a label container, a glue roller, a rotatable carrier provided with gluable withdrawing segments, and a gripper cylinder. Using such a labeling machine, it is possible to provide containers, such as bottles, with labels. The labeling machine can be configured, for example, as a rotary-table-type machine, a linear machine, or a horizontal-table-type machine. A label-position checking device is disposed in the exit area of the labeled bottles. The label position checking device monitors the desired orientation of the labels on the bottles.

It is known to check that a label is in a correct location relative to design features, such as embossings, on the bottles. It is also known to check neck and body labels for correct alignment, either relative to one another or to the design features. If a label's location deviates beyond a definable tolerance, the label position checking device conveys corresponding signals that trigger a correction device. The correction device then acts on the labeling units so that a correct label position can be achieved. The bottles that do not have a correctly positioned label are ejected via an outward transfer apparatus. The ejection can also take place as a result of the correspondingly generated signal of the label position checking device.

DE 44 41 245 A1 discloses a method for checking labeled vessels. The checking device, which is integrated in a labeling machine, is equipped with a laser distance meter. The laser distance meter can be used to determine whether or not a container has a label. During an active measuring interval the laser beam emitted by the laser distance meter first strikes the surface of a passing bottle and measures the latter's distance from its fixed-position housing. This position forms the constant point of reference.

As soon as the laser beam strikes the surface of the label, there is an abrupt decrease in the instantaneously measured distance. This abrupt decrease arises from and is equivalent to the thickness of the label and to the film of adhesive, if any, between the bottle and the label. This abrupt change of distance is captured in an evaluator and evaluated as a criterion for the presence of a label. Accordingly the evaluator sends either no signal or a signal indicating a good container to a sorting apparatus. If there is no label on the bottle, no abrupt change of distance can be detected. In such a case, the evaluator sends an error signal to the sorting apparatus, which then ejects the unlabeled bottle. This device can only tell whether a label is present on the bottle or not. It cannot determine whether the label is also correctly aligned relative to design features, or whether the label has creases.

DE 10 2006 022 492 A1 discloses a test container for a container checking device. The test container has many first marking rings that surround at least sections of the test container at predetermined, fixed heights. The test container also has many marking lines running in a longitudinal direction of the test container. The first marking rings are each disposed at constant, specified intervals in the longitudinal direction of the test container relative to one another. The marking lines intersect at least a part of the first marking rings. These marking lines are each disposed at predetermined intervals in a peripheral direction of the test container relative to one another. This is intended to facilitate a simplified adjustment of a camera to be changed in the checking device.

Bottles or similar containers are filled with a filling material by a filling apparatus, after which they are passed to a labeling machine. The containers are aligned either at the labeling machine or before they reach the labeling machine. In particular, the containers are aligned relative to design features so that the labels can be affixed to the containers with proper orientation relative to the design features. The labeled containers are again aligned and guided or conveyed past an inspection device that can be configured as a label position checker. If the label position checker detects containers with a bad or faulty label location, a signal for ejection is generated. The ejected containers are stored on a separate conveyor.

An inspection device, such as a label position checker, itself needs to be checked for correct operation. This can be done by checking the rejected containers. However this approach is very time-consuming and unreliable, in part because containers travel such high speeds. For example, many labeling machines have throughputs on the order of 16 containers per second. As a result, containers that were not rejected can only be checked randomly.

DE 10 2008 050 249 A1 relates to a test method for inspection devices, especially for label position checking devices. The test method described therein has proven to be advantageous in practice because the inspection device can be reliably checked for correct operation. The method adopted therein includes generating an individually predetermined number of test containers. These test containers are conveyed past the inspection device. If functioning correctly, the inspection device will also send a corresponding signal to an ejecting apparatus instructing it to eject at least faulty containers. An evaluator can of course be connected between the two devices. If the inspection device detects all faulty containers, and/or if all faulty test containers are ejected, and only fault-free test containers remain in the container flow, then one can infer that the inspection device is operating correctly.

According to DE 10 2008 050 249 A1, an individually predetermined number of test containers is generated manually. This means that the test containers are manually inserted into the container flow. If the test program is detected, at least the labeling function is switched off. The functional unit and/or labeling unit is automatically switched off when the test method is sequencing automatically. The test program can be run regularly, e.g. daily, before each shift change or before a product change.

The fact that only a low sampling depth can be achieved is a disadvantage because the test program is only run infrequently, for example once per shift. Manual interventions can result in increased operating errors. The issue of product liability in particular plays a part here, because a very great effort for documentation is required. A further disadvantage is that for example the labeling function is switched off when the test program is detected. However switching off the labeling function simultaneously involves a production interruption during the test and results in a loss of efficiency for the installation.

SUMMARY

An object of the invention is to provide a test method for examining an inspection device that avoids adversely affecting the performance of the treatment installation when the test method is being performed, and one in which performance of the test can be documented with less effort.

According to the invention the object is resolved by a test method comprising at least the generating a specified number of test containers by the functional unit itself, feeding a control signal for generating a distinctive element to the functional unit, and leading the test containers past the inspection device, which detects the test containers and ideally generates a control signal.

The correct operation of the inspection device can be reliably examined with the invention, without requiring intervention by an operator. Moreover the test method can be carried out without the functional unit having to be switched off. Because the examination of the inspection device is fully automated, a significantly reduced documentation effort is expected since all steps are effected automatically and each individual step is automatically consolidated at a suitable point and automatically archived or stored. The documentation can be retrieved at any desired time. The automatic test method is not bound by particular points in time such as shift changes, but can be carried out at any desired time, and preferentially at randomized times.

What is essential is that the specified number of test containers be generated by the functional unit itself so that automatic self-monitoring can be achieved. A master unit can typically be configured as a container treatment installation, such as a bottle treatment installation, that has functional units, such as a filler, a labeller, and/or a capper. However, these are examples only. Other functional units can be used.

When the functional unit is a filler, a distinctive element or defined error may be that a quantity that differs from the nominal quantity is filled into a container.

When the functional unit is a labeler, a defined error may for example be a label that has been applied in a skewed orientation.

When the functional unit is a capper, a defined error may be an incomplete capping.

Consequently an underfilling, an overfilling, a positional inaccuracy of the label, a missing label, a missing cap, too high a cap seating, too low a cap seating, and/or an incorrectly seated crown stopper may for example be generated as defined errors. These are specific examples only. Other distinctive elements or defined errors are also possible.

The invention is based on the knowledge that the functional units are each networked with the master unit or with the latter's control unit. The control unit can, for example, trigger the a functional unit such as the filler. Electronic fillers can trigger individual valves that generate the defined error. When the functional unit is a labeller, servo-driven stations can be selectively de-synchronized. The label feed at the dispenser station or the angle of rotation of the transport plate for the bottle carrier for example can be selectively triggered. When the functional unit is a capper, servo-driven capping elements can be selectively triggered.

The generating of the defined error is only carried out during the test method. It is an advantage that the control unit is networked with the error-generating functional unit so that the control unit knows and/or stores this error.

The inspection device connected downstream of the functional unit should detect the defined error and transmit an ejection signal to the corresponding ejecting apparatus. Alternatively a signal to eject the test container concerned is generated. However because the control unit knows the test container and is also networked with the ejecting apparatus, it is possible to establish whether the inspection device is operating correctly. For example, if the faulty test container were to reach the sorting apparatus and to remain in the container flow rather than being ejected, it is possible to infer a malfunction of the inspection device. The possibility of such malfunction can be announced by, for example, acoustic warning tones, or even an emergency stop at the offending functional unit to allow the inspection device to be manually examined.

It is also within the scope of the invention for the fully automatic test method for examining the inspection device to be carried out with good containers as well. In this case, the test method is started and no defined error or distinctive element is generated by the functional unit itself. The test container, with, for example, a correctly located label, is therefore conveyed past the inspection device. Because the control unit knows the position of the test container in the container flow, when the test container reaches the ejecting apparatus the control unit expects the ejecting apparatus to provide a signal that leaves the test container in the container flow. If the perfectly good test container is ejected, this also suggests a malfunction in the inspection device.

It is also essential to avoid switching off the particular functional unit whose associated inspection unit is to be examined. This is because the functional unit itself generates the defined error or the good test container. By the corresponding signal being transmitted to the functional unit, the latter can itself generate a single test container or a plurality of test containers as the specified or randomized number of test containers. Once the specified number of test containers has been generated, the functional unit can be returned directly to its normal mode upon receiving the corresponding signal.

The invention thus avoids the prior art practice of having to switch off the functional unit and then having to manually introduce the specified number of test containers into the container flow upstream of the functional unit.

Another disadvantage of the prior art method was that the test containers had to travel a relatively long distance until they reached the inspection unit that was to be examined. This consumed a considerable period of time during which the functional unit was switched off.

The invention on the other hand obviates the need for having to introduce test containers into the container flow at the inlet end. As a result, the testing procedure according to the method described herein is one of relatively short duration, being naturally dependent on the random number of test containers. The test container is preferentially generated by the functional unit itself in a randomized manner from a random container in the container flow.

A specified number of test containers which are conveyed past the inspection device is therefore advantageously generated. If functioning correctly, the inspection device should also send a corresponding signal to the ejecting apparatus instructing it to eject at least faulty containers. An evaluator can be connected between the two devices. If the inspection device detects all faulty containers, and/or if all faulty test containers are ejected, and if it leaves fault-free test containers in the container flow, then the inspection device is operating correctly.

In a preferred embodiment, the inspection unit inspects the test container or test containers and generates a measured value by means of which the number of test containers with defined error can be determined. The variance between the nominal measured value and the actual measured value can be determined by means of the measured value. Ideally, the nominal measured value is the specified number of test containers with defined error, i.e. the number of test containers that is stored in the control unit, and the actual measured value is the number of test containers with defined error as measured or captured by the inspection device.

In some practices of the invention, the inspection device generates a signal for ejecting at least those test containers with defined error.

In any test method or test program, a different number of faulty test containers can also be generated by the functional unit itself, which is what is meant by the term "randomized number." It is also advantageous for the inspection devices to be examined simultaneously. For example, when the functional unit is labeler, the labeler could generate a label location that is not aligned on embossings while at the same time the respective functional unit, which is a filler, generates an underfilling at the same test container, and a capper generates an incorrect capping of the same test container. This is possible because the control unit knows the position of the test container concerned and can therefore trigger the respective functional units and verify whether the particular inspection device generates the corresponding control signal. In this way a test container is advantageously generated with the defined error by the respective functional unit, such that the number of test containers that must be ejected is reduced, which has the beneficial effect of reduced rejects and increased efficiency. Different test containers can of course also be generated by the particular functional unit itself, thereby generating a test container flow.

It is also essential that the test method be carried out in a randomized manner. This means that all or part of the inspection units can be examined in a randomized manner simultaneously or at random times independently of one another. If all or part of the inspection units are examined in a randomized manner simultaneously, then examination can begin with the first functional unit/inspection unit upstream. This means that when the first functional unit upstream is duly randomly triggered to generate the distinctive element/defined error, the randomization of the others is disabled, and can be triggered to generate the defined error. As an alternative, randomly determined, sequence is equally possible.

If it is operating correctly, the inspection device should detect the faulty test containers. A signal for ejecting the faulty containers would then be generated in a known manner.

As already suggested above, for the further examination of the inspection device or label position checker, provision can also be made for at least one good container to be conveyed past the inspection device as a test container. If the inspection device is operating correctly, the good container should either not be ejected or be preferentially ejected but identified as being a good container.

In a preferred embodiment of the method, provision can be made to create a combined test container flow of the functional unit concerned and/or of all and/or of some of the functional units. The flow comprises a randomly specified number of faulty and non-faulty test containers. For example, the flow can be a combined test container flow from, for example, correctly labeled and incorrectly labeled, and/or underfilled or overfilled and correctly filled containers, and/or incorrectly and correctly capped test containers. This combined test container flow is conveyed past the inspection devices. If the inspection device concerned is operating correctly, the fault-free test containers remain in the test container flow, and the faulty test containers are ejected. Alternatively, the fault-free test containers can be ejected but then identified as being in order.

The invention provides a test method for the self-checking of an inspection device, which in the preferred embodiment as a label position checking device. By this test method an examination of the correct operation of the inspection device can be carried out reliably. A plurality of test runs, for example per shift, is also possible.

In a preferred embodiment, the inspection device can be connected to an inspection screen so that the result is displayed as soon as the containers have passed by the inspection device. This permits a judgement on the correct operation of the inspection device to be directly made at the same time.

It is also important that examinations other than only a visual examination be possible, since the position of the test container provided with the defined error, or of the error, is known, such that an automatic self-monitoring is advantageously made available. This self-monitoring requires no operator intervention, which of course avoids not only the operating itself but substantial operator costs as well. A benefit that is not to be underestimated is the constantly uniform and consistent quality of examination. This reduces error sources arising, particularly operator errors. Execution is fully automatic with no intervention on the part of the operator.

The test method permits clear and documented rules for the method and the test results. These rules ensure, or at least greatly simplify a quality control, thus reducing risk of product liability.

Once the test containers have been generated by the functional unit itself, the functional unit is automatically returned to its original function.

The invention is suitable in preferred applications for any inspection machines/apparatus and monitoring machines. To this extent the inventive test method can be implemented, for example on labeling machines for verifying the label location and for an embossing alignment check so as to allow the owner-operator of the labeling machine to establish, at any time, whether the inspection machine is operating correctly or whether, for example, maintenance work and/or adjustments are necessary. In particular the inventive test method can also be used on other inspection devices in order to verify their correct operation by means of a specified number of bad containers and good containers.

In one aspect, the invention features a test method for examining an inspection device associated with a functional unit of a master unit. Such a method includes generating a specified number of test containers, by the functional unit itself, by feeding, to the functional unit, a control signal for generating a distinctive element, and leading the test containers past the inspection device, which detects the test containers and generates a control signal.

Practices of the invention include those in which generating the test containers comprises generating them in a randomized manner. As a result, the test method is carried out at randomized times.

In some practices, the master unit is selected to be a bottle treatment installation, and the functional unit is a filler, a labeling machine, or a capper.

Further practices of the invention include those in which generating test containers comprises filling a container with a quantity of content that deviates from a nominal quantity, those in which it comprises causing a container to have a labeling error selected from the group consisting of an incorrectly applied label and a missing label, and those in which it comprises causing a container to have a capping error selected from the group consisting of an incorrectly applied cap and a missing cap.

In some practices, the master unit is in network communication with the functional unit.

Other practices include randomizing the specified number of test containers.

In yet other practices, the functional unit remains in operation while the inspection device inspects the test containers.

Some practices of the invention also include leading a randomized number of test containers past the inspection device. In these embodiments, the inspection device generates a signal for ejecting faulty test containers. Other practices include leading a randomized number of test containers with no distinctive element or defined error past the inspection device, said test containers remaining in the container flow.

In certain practices, generating a specified number of test containers, by the functional unit itself, comprises generating a combined test container flow, the flow having a randomized number of faulty and fault-free test containers. In these practices of the invention, leading the test containers past the inspection device comprises leading the combined test container flow being past the inspection device concerned. The inspection device then generates a signal for ejecting faulty test containers. As a result, fault-free test containers remain in the test container flow.

Some practices of the invention also include automatically returning the functional unit to normal function after generating the randomized number of test containers with the distinctive element or with the defined error.

Additional practices carry out certain procedures in response to detecting an error. These include automatically correcting the error and minimizing possible damage resulting from the error and/or automatically providing information on corrective action and on the automatically initiated correction of the error.

BRIEF DESCRIPTION OF THE DRAWINGS

The advantages of the invention can be established by reference to data mentioned by way of example only and having no limiting effect, a purpose that flowcharts in the accompanying figures are intended to serve, in which.

DETAILED DESCRIPTION

Figure 1:
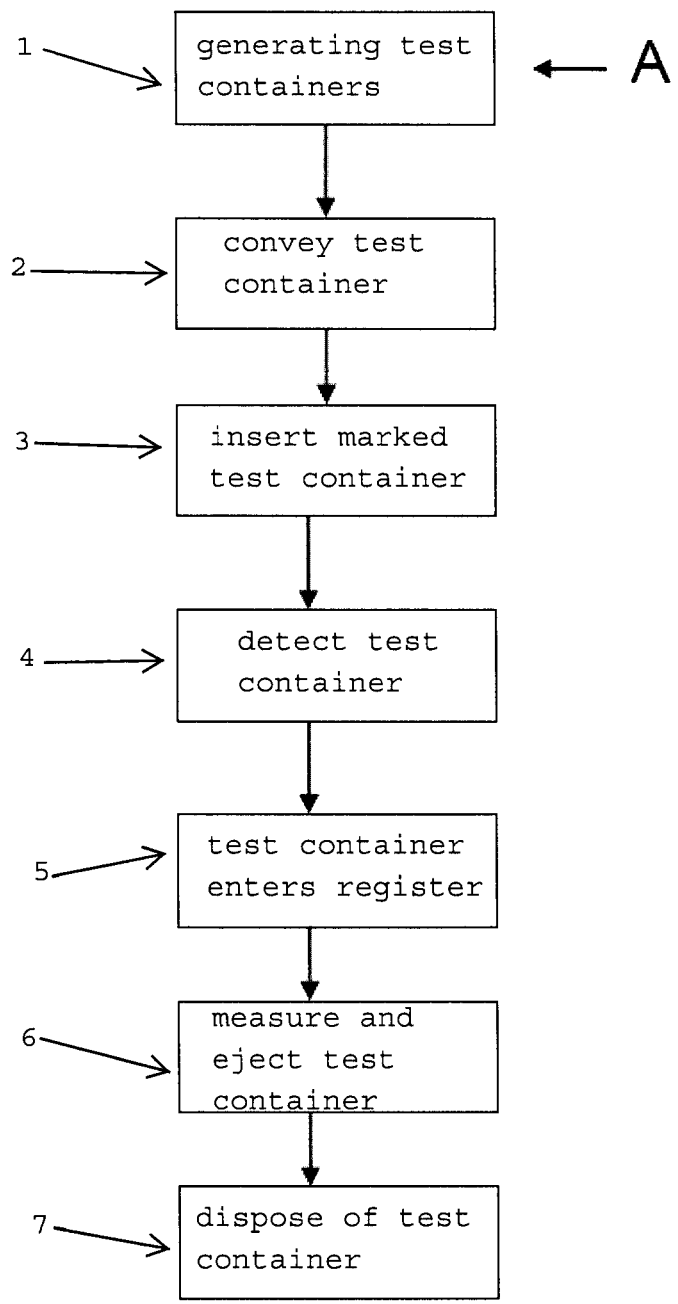
FIG. 1 shows a test method according to the prior art.

In FIG. 1, flowchart A discloses a test procedure that starts at block 1 when an operator or a laboratory generates an individually specified number of test containers. A manufacturing time of, for example, three minutes is allocated for this.

At block 2, the operator conveys the test containers that were generated in block 1 to, for example, a labeling machine. This can take about five minutes. The test method is only started when the test containers are manually introduced into the container flow.

At block 3, a marked test container is placed in front of the test containers so that the start of the test program can be verified. Details of this procedure are described in DE 10 2008 050 249 A1, which is incorporated herein by reference. Typically, a time of, for example, thirty seconds is allocated for block 3. During this interval, the risk of a production stoppage or production interruption can be considerable.

At block 4, the test container is supposed to be detected by the sensor system. However there can be an attendant risk of a minimal sensor system that fails to detect the container.

At block 5, the detected test container is entered in a register.

At block 6, the test container is measured and positively ejected.

At block 7, the test container is disposed of.

Blocks 4 to 7 are assumed to require another thirty seconds.

In all therefore, nine minutes are needed to carry out the method illustrated in FIG. 1. During this period, the operator is engaged on activities that are alien to his usual tasks.

Figure 2:
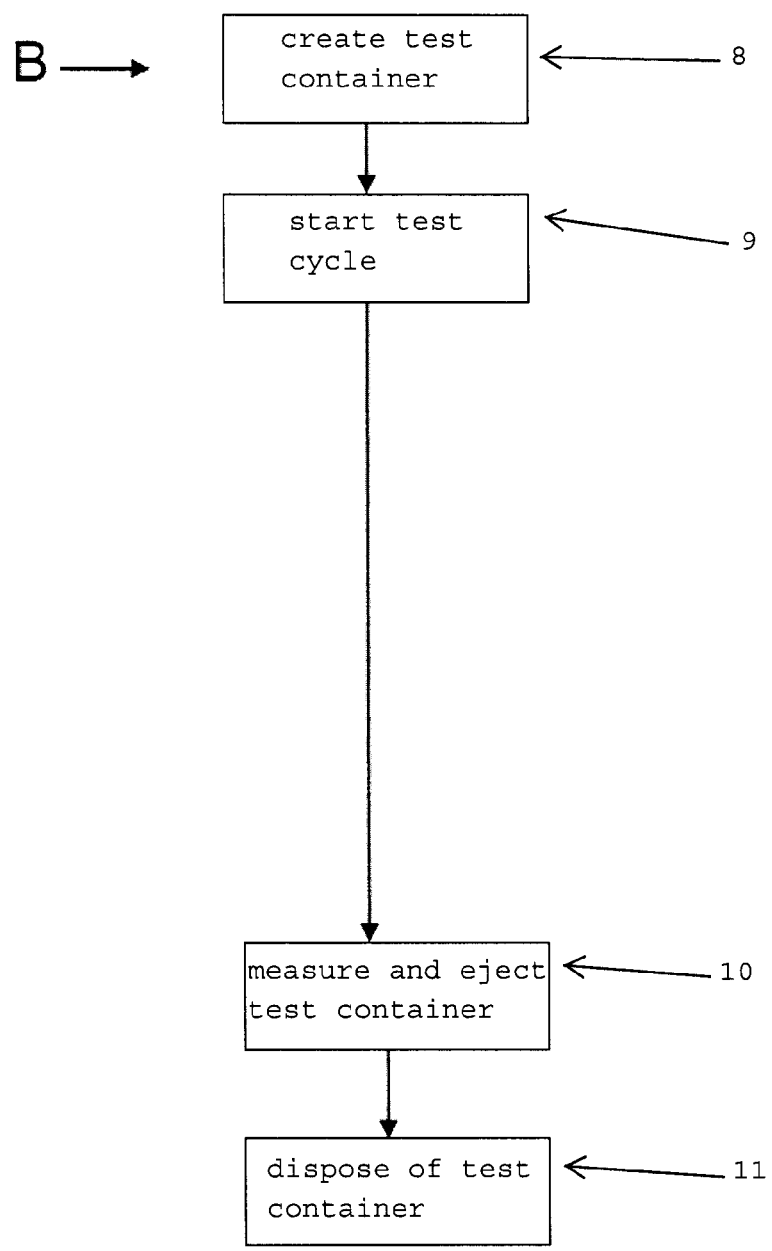
FIG. 2 shows a procedure according to the present invention.

FIG. 2 illustrates, in flowchart B, an alternative inspection method.

At the start of the examination of the inspection device in block 8, the functional unit itself generates a desired error on a container taken at random from the container flow, thereby creating the test container. The desired error is created by an appropriate instruction carried by a signal to the functional unit. The location, i.e. the site, and the error, are unique. Unlike block 1 in flowchart A, no time is lost in block 8 because the desired error is automatically generated by the functional unit itself.

At block 9, the system starts autonomously and fully automatically with its test cycle.

At block 10, the test container is measured and positively ejected.

At block 11, the test container is disposed of. Blocks 10 and 11 thus correspond to blocks 6 and 7 in flowchart A. As with flowchart A, a time of thirty seconds is assumed for blocks 10 and 11.

It can be seen that flowchart B contains no blocks equivalent to blocks 3, 4 and 5. As a result, a time advantage of thirty seconds is gained by eliminating the original steps according to blocks 3 to 5 in flowchart B.

An additional advantage is that is that in blocks 8 and 9, no operator time accrues because the procedure is fully automatic. As a result, there is an advantage of three minutes over block 1 of flowchart A and a time advantage of five minutes over block 2 of flowchart A.

Flowchart B thus saves three minutes avoiding the work at block 1, five minutes avoiding the work of block 2, and another half-minute avoiding the work of blocks 3-5. This provides an overall time gain of 8.5 minutes over the method shown in flowchart A. Assuming an hourly wage rate of EUR 40, this would result in a saving on operator costs of approximately EUR 3400 per year.

Another way to look at the advantage of the method shown in FIG. 2 is to recognize that instead of the three examinations carried out according to the method shown in flowchart A, seventeen test methods could be carried out with the procedure according to flowchart B for the same cost. With the inventive procedure according to flowchart B therefore, more sampling can be carried out for the same cost.

In addition, the method described in FIG. 2 inherently allows clear and simple documentation to be created. If the inspection unit does not operate correctly, an error message is automatically generated. This reduces error reporting and/or error tracing time and results in an overall shorter response time.

Yet another advantage is that the method shown in FIG. 2 avoids interrupting production. This means that there is less loss of efficiency because the functional unit is not switched off while the test method is in progress.

Having described the invention, and a preferred embodiment thereof, what is new and secured by Letters Patent is:

1. A test method for examining an inspection device associated with a functional unit of a master unit, said method comprising:
generating a specified number of test containers, by the functional unit itself, by feeding, to the functional unit, a control signal for generating a distinctive element; and
leading the test containers past the inspection device, which detects the test containers and generates a control signal.

2. The test method of claim 1, wherein generating the test containers comprises generating the test containers in a randomized manner, whereby the test method is carried out at randomized times.

3. The test method of claim 1, further comprising selecting the master unit to be a bottle treatment installation, and selecting the functional unit from the group consisting of a filler, a labelling machine, and a capper.

4. The test method of claim 1, wherein generating test containers comprises filling a container with a quantity of content that deviates from a nominal quantity.

5. The test method of claim 1, wherein generating test containers comprises causing a container to have a labeling error selected from the group consisting of an incorrectly applied label and a missing label.

6. The test method of claim 1, wherein generating test containers comprises causing a container to have a capping error selected from the group consisting of an incorrectly applied cap and a missing cap.

7. The test method of claim 1, wherein the master unit is in network communication with the functional unit.

8. The test method of claim 1, wherein the functional unit remains in operation while the inspection device inspects the test containers.

9. The test method of claim 1, further comprising leading a randomized number of test containers past the inspection device, and wherein the inspection device generates a signal for ejecting faulty test containers.

10. The test method of claim 1, further comprising leading a randomized number of test containers with no distinctive element or defined error past the inspection device, said test containers remaining in the container flow.

11. The test method of claim 1,
wherein generating a specified number of test containers, by the functional unit itself, comprises generating a combined test container flow, the flow having a randomized number of faulty and fault-free test containers, and
wherein leading the test containers past the inspection device comprises leading the combined test container flow being past the inspection device concerned, the inspection device generating a signal for ejecting faulty test containers, whereby fault-free test containers remain in the test container flow.

12. The test method of claim 1, further comprising randomizing the specified number of test containers.

13. The test method of claim 12, further comprising automatically returning the functional unit to normal function after generating the randomized number of test containers with the distinctive element or with the defined error.

14. The test method of claim 1, further comprising, in response to detecting an error, automatically correcting the error and minimizing possible damage resulting from the error.

15. The test method of claim 14, further comprising, in response to detecting an error, automatically providing information on corrective action and on the automatically initiated correction of the error.

* * * * *